United States Patent
Albano

(10) Patent No.: US 7,374,750 B2
(45) Date of Patent: May 20, 2008

(54) PROBIOTIC CONTAINING ANHYDROUS HAIR CARE COMPOSITION

(76) Inventor: Jennifer Albano, 389 Union St., Brooklyn, NY (US) 11231

(*) Notice: Subject to any disclaimer, the term of this patent is extended or adjusted under 35 U.S.C. 154(b) by 189 days.

(21) Appl. No.: 10/845,931

(22) Filed: May 14, 2004

(65) Prior Publication Data

US 2005/0255070 A1    Nov. 17, 2005

(51) Int. Cl.
*A61K 8/00* (2006.01)
*A61K 8/72* (2006.01)
*A61K 8/64* (2006.01)

(52) U.S. Cl. ............. 424/70.1; 424/70.11; 424/70.14

(58) Field of Classification Search ............... None
See application file for complete search history.

(56) References Cited

U.S. PATENT DOCUMENTS

| | | | |
|---|---|---|---|
| 2,261,094 A | | 10/1941 | Speakman |
| 4,205,132 A | | 5/1980 | Sandine et al. |
| 4,460,571 A | * | 7/1984 | Gomez .................... 424/70.14 |
| 4,605,108 A | | 8/1986 | de la Guardia et al. |
| 5,597,558 A | | 1/1997 | Aubert et al. |
| 5,811,111 A | * | 9/1998 | McAtee et al. ............. 424/401 |
| 6,162,775 A | * | 12/2000 | Methmanus-Spaltro ..... 510/130 |
| 6,258,355 B1 | * | 7/2001 | Cavaliere widow Vesely et al. ........................ 424/93.45 |
| 6,270,811 B1 | | 8/2001 | Fregonese |
| 6,376,455 B1 | * | 4/2002 | Friedli et al. ............... 510/515 |
| 6,444,196 B1 | | 9/2002 | Evans |
| 6,455,058 B1 | | 9/2002 | Sun et al. |
| 6,531,126 B2 | * | 3/2003 | Farmer ....................... 424/115 |
| 6,656,457 B2 | | 12/2003 | Kamis et al. |
| 2003/0031659 A1 | * | 2/2003 | Farmer .................... 424/93.45 |

FOREIGN PATENT DOCUMENTS

| | | | |
|---|---|---|---|
| JP | 04026613 | * | 12/1999 |
| PL | 176077 | * | 5/1994 |

OTHER PUBLICATIONS

M. Kimura et al. (2002). "Simultaneous contact sensitivity to hydroxystearic acid and C18-36 acid triglyceride in lip gloss," Contact Dermatitis vol. 47, p. 115.*
Definition of "polyethylene glycol," Hawley's Condensed Chemical Dictionary, 14th Edition, John Wiley and Sons, Inc. 2002.*
Definition of "anhydrous," Hawley's Condensed Chemical Dictionary, 14th Edition, John Wiley and Sons, Inc. 2002.*
Kononenko et al., Izvestiya Akademii Nauk SSSR, Seriya Biologicheskaya 6 : 869-78 (1977), abstract only.*
Patricia Siuta-Cruce & Jacques Goulet, "Improving Probiotic Survival Rates." FoodTechnology, Oct. 2001, vol. 55, No. 10, pp. 36-42. Institute of Food Techns., Chicago, USA.
Chr. Hansen Customer Web Center, https://www.mychr-hansen.com/webapp/wcs/stores/servlet/CategoryDisplay?storeId=10001&langId=-101&catalogId=10101&categoryId=10393&path=10251,10279,10393 (2007).
Hany Khalil and Rafael Jimenez-Flores, Cal. State Univ. Agricultural Research Initiative, Project No. 06-3-17: *Mechanisms of Protection and Intestine Colonization of Probiotic Bacteria Offered by Milk Fat Globule Membrane in Yogurt as Determined by Laser Tweezers*, http://ari.calstate.edu/research/index.aspx?Transform=Details&ProjectNumber=06-3-017, (2007).
Product Range; http://www.lallemand.dk, (2007).
*Institut Rosell Combines Probiotics and Chocolate*; http://www.vpico.com/articlemanager/printerfriendly.aspx?article=87416, Copyright 2007 by Virgo Publishing, http://www.naturalproductsinsider.com/ Posted on: Jul. 18, 2005.
*Probiotic technology wins award*; http://www.foodnavigator.com/news/printNewsBis.asp?id=43565, Mar. 27, 2002.
Crittenden, Ross, et al, *Synbiotic Microcapsules That Enhance Microbial Viability during Nonrefrigerated Storage and Gastrointestinal Transit*, Applied and Environmental Microbiology, Mar. 2006, p. 2280-2282, vol. 72 (3).
Ying-H. Sheih, MD, et al., *Systemic Immunity—Enhancing Effects in Healthy Subjects Following Dietary Consumption of the Lactic Acid Bacterium, Lactobacillus rhamnosus HN001*, 20 J. Amer. College Nutrition 20,149-156 (2001).
G.W. Tannock, et al., *Analysis of the fecal microflora of human subjects consuming a probiotic product containing Lactobacillus rhamnosus DR20*. App. Environ. Microbiol. Jun. 2000; 66 (6): 2578-2588 (Amer. Society for Microbiology); http://www.pubmedcentral.nih.gov/articlerender.fcgi?artid=110584.
Dewald, Robert R., *Preservation of Serratia marcescens by High-Vacuum Lyophilization*, Applied Microbiology, Jul. 1966, vol. 14 (4) : 561-567.

* cited by examiner

*Primary Examiner*—Sandra Saucier
(74) *Attorney, Agent, or Firm*—Morgan, Lewis & Bockius LLP; Pristine Johannessen, Esq.

(57) ABSTRACT

This invention concerns nutritive and restorative hair care compositions which are distinctive in that they contain probiotic bacteria and other ingredients found in yogurt. Both water-based and anhydrous embodiments are described. The compositions are designed to moisturize, soften, condition, straighten, strengthen and repair hair in addition to promoting a healthy scalp.

11 Claims, No Drawings

PROBIOTIC CONTAINING ANHYDROUS HAIR CARE COMPOSITION

BACKGROUND OF THE INVENTION

It is widely known that yogurt contains potent ingredients that are beneficial to overall human health and well-being. Over the centuries and in many regions of the world, yogurt has been and remains an integral and nourishing dietary staple. It is particularly beneficial to digestion and a healthy digestive tract.

Yogurt is created from milk using a heat fermentation process that incorporates the use of certain bacteria to effectively curdle the milk into a more concentrated and thick form. After the fermentation process is complete, some of the bacterial cultures usually survive. They remain in the yogurt providing considerable benefits upon ingestion. It is known that such "probiotic" bacteria themselves aid in digestion, counter the detrimental effects of non-beneficial bacteria and prevent certain kinds of digestive problems. It is further known that certain probiotic material can be used to create yogurt from milk. In addition, most known nutritional yogurt products are often supplemented with other live, active and beneficial, probiotic bacteria.

Yogurt can be used topically on hair in certain ways with considerable benefit. See U.S. Pat. No. 4,268,500 to Cloninger. Much like the milk from which yogurt is derived, yogurt contains particular proteins and a significant amount of lactose. In addition, both yogurt and milk contain emollient properties that contribute to healthy and attractive hair.

Two proteins which exist in yogurt and are likely to be responsible for its benefits to hair are casein and whey. Casein is present in yogurt as a by-product of the fermentation by the lactic acid-producing cultures (William Helferich and Dennis Westhoff in *All About Yogurt*, Prentice Hall, Inc. NJ, 1980). Casein has structural similarities with fibrinogen aside from of the fact that both are proteins with different physiological functions. While casein forms polymeric globules (micelles), fibrinogen is a fibrous polymer. An analogy between fibrinogen and casein has been reported by Jolles P., et al. in *Analogy Between Fibrinogen and Casein and Effect of an undecapeptide isolated from kappa-casein on platelet function*. Europ. J. Biochem. 158, 379-82. Fibrinogen produces molecular aggregation and the formation of a protective coating over damaged cells. Fibrinogen is a fibrous protein; it is stringy, tough and insoluble in water. Casein is a globular protein; it has a spherical shape. Alpha-keratin, the protein in hair and nails, has an alpha-helix structure. Casein and fibrinogen are similar in that fibrinogen is composed mostly of alpha-keratin, while the secondary structure of casein involves both alpha-helix and beta-sheet shapes. As healing and restorative processes progress, fibrinogens specifically form covalent bonds between the fibrin monomers. Casein present in yogurt could produce the same effect (formation of covalent bonds) due to the presence of the alpha-helix and beta-sheets shapes present in its secondary structure. Casein is a mixture of several similar phosphoproteins: alpha, beta, lambda and kappa-casein, all of which contain some serine side chains combined with phosphoric acid.

If we compare milk to yogurt, milk contains unprecipitated casein, while yogurt's casein is precipitated. Thus the number of peptides present in milk is much less than the number of peptides present in yogurt. Therefore, contrary to widespread industry assertions, the number of kappa-casein peptides present in milk are unlikely to deliver significant conditioning effects. Further, another difference between casein present in milk and precipitated casein in yogurt is the ability to form aggregates in the presence of charged surfaces. Casein in milk at pH 6-7, contains charged surfaces (chiefly negative charged phosphoserine residues) which repel each other. However, reduction of the pH in casein in yogurt to a pH of less than 5, reduces the ionization of serine phosphate residues and encourages agglomeration. Agglomeration is the first step leading to intermolecular and intramolecular cross links.

Whey is another protein found in milk and yogurt. Whey protein is rich in certain amino acids and low in fat. The key amino acids, the branched chain amino acids (e.g. leucine, valine and isoleucine) and cysteine can be found in relatively high amounts in whey protein (up to 3 g/100 g of protein). Whey proteins can differ dramatically from one another depending on the processing method and the total protein content. For example, whey protein can exist as simple whey powder (30% or less total protein content), whey protein concentrate (30-85% protein) or whey protein isolate (90% or higher protein content).

Whey protein is composed of alpha-lactalbumin, betta-lactoglobulin, serum albumin, immunoglobulins and protease peptones. Betta-lactoglobulin (BLG) is the dominant whey globular protein found and secreted in bovine milk. BLG is predominantly dimeric, consisting of two identical unit configurations of 162 residue sequence. BLG provides numerous sites for sulphidryl groups to form.

Although there appears to be no real distinction between curly hair and straight hair substructurally or chemically, there may be a difference in the geometric distribution of orthocortical and paracortical cells or in the shape of the hair follicle. In addition, the differences may be in variable ratio between crystalline and amorphous materials in the hair. Keratin is the principle structural protein of hair, providing its structural integrity. It is composed of eighteen different amino acids and is characterized by the presence of cystine and the absence of hydroxyproline. Keratin is held together by several different kinds of polypeptides bonds such that proteolytic enzymes (i.e., enzymes that break apart, or lyse, protein molecules) do not attack it. The great stability of keratin results from the numerous disulfide bonds of cystine. Hair keratin is insoluble in aqueous salt solutions, weak acids, weak alkalis and neutral solutions. Water can, however, alter its appearance. This is evident when wet hair is set. It will hold the set when it dries, but this change is temporary and will disappear when the hair becomes wet again.

Cystine may account for 24 percent of the total amino acids. The cystine in keratin contains disulfide linkages—the bonds responsible for the strength and structure of natural keratin of hair and nails. Reduction of the disulfide bonds (by thioglycol or some other mild reducing agent) to sulfhydryl groups, results in dissociation of the peptide chains. The presence of these disulfide bonds makes permanent hair conditioning possible. Permanent hair conditioning occurs through a mechanism known as disulfide interchange, a reaction in which cystine-containing proteins covalently bond and form a disulfide link with free sulfhydryl (SH) groups in the hair.

The manufacture of structural soluble keratin-type molecules by cosmetic material suppliers is achieved by the hydrolyzation methods. These methods use very high temperatures and extreme conditions that can convert cystine to cysteic acid (a reaction analogous to the effect of damage in hair). Milk fermentation based on the inoculation of cultures provides a more natural, gentle process and less of a possibility of the conversion of cystine to cysteic acid.

Cystine containing proteins can also help protect, strengthen and extend the life of cosmetic chemical hair treatments by reducing "unzipping", a term used to describe the tendency of reconfigured SH groups to return to the original position. This can occur when one SH group reacts with a neighboring SH group, thereby breaking the S—S linkage to reform the original S—S bond and leaving a different free SH group available. This initiates a chain reaction in which each subsequent free SH group that becomes available reacts with the next S—S bond adjacent to it. Thus, by covalently bonding with residual SH groups left in the hair after a chemical treatment, these proteins are able to "tie-up" or block free SH groups and lessen the incidence of unzipping.

Within the art, it is further known that the bacteria such as *Lactobacillus bulgari* and *Streptococcus thermophilus* are necessary ingredients for the creation of yogurt. Other yogurt cultures exhibit marked nutritive and restorative effects and are thus in demand as probiotics in yogurt mixes including, but not limited to, *Lactobacillus acidophilius*, *Lactobacillus reuteri* and *Bifidobacteria*. It has been found that some of these bacteria survive the fermentation process used to form yogurt from milk and provide benefits in addition to those found in the yogurt itself. These bacteria participate in competitive inhibition in the human intestinal tract, where they beat out "bad," possibly pathogenic microorganisms for nutrients and space. See *The Dominant Culture: Yogurt for the Masses*, by Kimberly J. Decker, April 2001. It is an aspect of this invention that these bacteria could have similar beneficial effects on hair, which is exposed to numerous bacterial agents throughout a normal day.

The stability of probiotic cultures is also addressed by this invention. In many products containing probiotics that are developed and sold for consumption, active cultures die even before the consumer receives any of the health benefits (i.e., during manufacturing, during storage, or during transport of the finished product). Even if the probiotics stay alive during manufacturing, they must also have sufficient shelf life to be viable when ultimately used. Specifically, probiotics are extremely susceptible to their environment. Such environmental factors as water, oxygen, temperature, and acidity affect the overall viability of these beneficial microorganisms. See, e.g., Patricia Siuta-Cruce and Jacques Goulet, "Improving Probiotic Survival Rates." Food Technology, October 2001, Vol. 55, No. 10, Pp. 36-42. This problem is addressed in the anhydrous formulation embodiment which is intended to maintain essentially water free conditions to keep the probiotic bacteria more viable prior to usage.

It is the intention of this invention to teach the benefits of using yogurt and components of yogurt in novel hair care compositions that take advantage of the beneficial properties of yogurt, components of yogurt and probiotic bacteria. The compositions taught herein will promote healthy hair 1) by cleaning, repairing and smoothing damaged hair, 2) by promoting a healthy scalp and 3) through a bacterial cleansing of clogged hair follicles. It is suggested by the inventor that the benefits of probiotic bacteria will extend to cleaning and regeneration of the sebacious gland and hair follicle itself by competing with non-beneficial bacteria to promote strong hair growth.

SUMMARY OF THE INVENTION

This document describes the effects of the use of several compositions when used over certain periods of time. It also contains various examples of embodiments in which yogurt, yogurt components and/or live bacteria are used in combination with various mixtures of known ingredients that have beneficial effects on hair. These combinations create surprising and novel innovations in hair care.

Within the context of the present invention, several compositions comprised of both known hair care ingredients and components of yogurt (including extracts of whey, casein and probiotic bacteria) have been manufactured and tested. The results herein, demonstrate surprisingly effective hair treatments.

One of the compositions manufactured is composed of only anhydrous ingredients. This composition is special in that it provides a non-aqueous environment for the probiotic bacterial components thereby preserving the activity of these bacteria when they are applied to wet hair. It is known that probiotic bacteria, when exposed to water, have a very short shelf life. By using an anhydrous composition—i.e. one that contains no water or water based ingredients—the probiotic ingredients should remain active indefinitely. Exposure to water, as in a shower or bath where the hair care compositions contemplated in this patent are to be used, the full benefits of the probiotic ingredients will be attained. Keeping the bacteria away from water allows them to remain viable, and thus available for beneficial affect on both hair and scalp at the time of application. See *Dairy Industries International*, January, 1998, No. 1, Vol. 63; Pg. 25.

Tests performed to date have shown that the compositions disclosed herein promote healthy hair. The compositions all moisturize, soften, condition, straighten, repair, promote a healthy scalp and promote strong hair growth. Another surprising result is that after the application of the compositions disclosed herein, the time taken to blow hair dry is significantly reduced. Other surprising results are 1) the creation of a barrier against environmental stresses between applications and 2) a cumulative benefit resulting in hardier hair.

The invention contemplates the addition of probiotic bacteria other than those initially in the yogurt making process.

DESCRIPTION OF THE PREFERRED EMBODIMENTS

The components of this invention can also be mixed with other cosmetically or pharmaceutically acceptable excipients, as is understandable to a one skilled in the art. Other aims, characteristics and advantages of the invention will emerge in light of the explanatory description which will be made with reference to several examples of compositions as well as various tests which have been carried out. In the examples, all the percentages are given by weight and the temperature is ambient temperature and the pressure is atmospheric, unless otherwise indicated.

EXAMPLE #1

Anhydrous Self Heating Yogurt Hair Mask

TABLE 1

| Seq. | INCI Name | Trade Names | % W/W |
|---|---|---|---|
| 1 | PEG 200 | PEG 200 | 71.96 |
| 1 | Glycerin | Glycerin | 5.00 |
| 1 | Stearamidopropyl Dimethylamine | Incromine SB | 2.00 |

TABLE 1-continued

| Seq. | INCI Name | Trade Names | % W/W |
|---|---|---|---|
| 1 | Behentrimonium Chloride | Incroquat Behenyl TMC-85 | 2.00 |
| 1 | Stearyl Alcohol | Stearyl Alcohol | 1.50 |
| 1 | Behenyl Alcohol | Behenyl Alcohol | 1.50 |
| 1 | Glyceryl Stearate SE | Lipo GMS 470 SE | 1.00 |
| 1 | Stearic Acid | Stearic Acid | 1.00 |
| 1 | Olea Europaea (Olive) Fruit Oil | Olive Oil | 0.50 |
| 1 | Dimethicone | DC 200/100 | 0.50 |
| 2 | Whey Protein Concentrate | Alacen 841 | 0.30 |
| 2 | PEG 200 | PEG 200 | 11.50 |
| 2 | Papain | Papain | 0.02 |
| 2 | Panthenyl Hydroxypropyl Steardimonium Chloride | Panthequat | 0.05 |
| 2 | Non-Fat Dry Milk | Dry Milk | 0.10 |
| 2 | Olea Europaea (Olive) Leaf Extract | Eurol BT (Presperse) | 0.01 |
| 2 | Ascorbic Acid | Vitamin C | 0.01 |
| 2 | Fragrance | Linden/Relaxing MF-106381 Mane | 0.15 |
| 2 | Citrus Aurantifolia (Lime) Oil | Lime Oil Manheimer #01920 | 0.05 |
| 2 | Fragrance | Gardenia Manheimer #858299 | 0.60 |
| 3 | *L. rhamnosus, L. casei, L. plantarum, L. acidophilus, B. longum, B. breve, Pediococcus, Acidilactici, Lactococcus diacetylactis,* | Bacteria | 0.05 |

The first embodiment is an anhydrous formulation with ingredients and percent weight as set forth in Table 1. The process of making the anhydrous formulation is as follows:

In stainless steel, jacketed kettle, equip with Lightnin' type (propeller with adjustable rate) agitation and sweep agitation, combine Seq. 1 materials and begin heating under Lightnin' type agitation to 80-82 C. so all ingredients melt into the mixture. When batch is uniform, begin cooling under agitation to 42 C. Switch to sweep when necessary or as batch thickens. At 42 C. begin adding Seq. #2 materials one at a time under adequate mixing, being sure each is well mix before continuing. Cool to 25 C. Add Seq. #3 bacteria complex and mix batch until uniform.

The final anhydrous formulation's Initial Viscosity as measured using a Brookfield LVT Spindle #4 @ 6 RPM's for 1 minute=53,200 cps Dial Reading 55%. It appears as a white to off white opaque cream and has an odor that is a slightly floral with citrus note. Its specific gravity measures 0.927 (+/−0.03) when measured using a Stainless Steel grease Pychnometer @ 25 degrees Centigrade.

EXAMPLE # 2

Hydrous Formulation

TABLE 2

| INGREDIENTS | C.T.F.A. NAME | % W/W |
|---|---|---|
| 1- Distilled Water | 1- Deionized Water | 62.45 |
| 2- Cellosize HEC 52000H | 2- Hydroxyethylcellulose | 1.30 |
| 3- Alacen 841 | 3- Whey Protein Concentrate | 0.30 |
| 4- Kytamer PC | 4- Chitosan PCA. (A natural derivatives of crustacean shells. Completely Biocompatible.) | 0.15 |

TABLE 2-continued

| INGREDIENTS | C.T.F.A. NAME | % W/W |
|---|---|---|
| 5- Glucquat 125 | 5- Lauryl Methl Gluceth - 10 Hydroxypropyl Dimonium Chloride. | 10.00 |
| 6- Promulgen D | 6- Cetearyl Alcohol & Ceteareth-20 | 4.50 |
| 7- Stearyl Alcohol | 7- Stearyl Alcohol, NF | 0.50 |
| 8- Cetyl Alcohol | 8- Cetyl Alcohol, NF | 0.75 |
| 9- Lambent F-100 | 9- Dimethicone | 4.00 |
| 10- Incroquat Behemyl TMS | 10- Behentrimonium Methosulfate & Cetearyl Alcohol | 5.00 |
| 11- Abil OSW-12 | 11- Cyclomethicone/ Dimethiconol/ Dimethicone | 0.50 |
| 12- Brij 72 | 12- Steareth-2 (Polyoxyethylene 2 Stearyl Ether) | 0.50 |
| 13- Tritisol | 13- Hydrolyzed Wheat Protein | 2.50 |
| 14- Cetylsil Basics | 14- Cetyl Triethylmonium Dimethicone copolyol Phthlate | 3.00 |
| 15- D.C. 929 Cationic Emulsion | 15- Amodimethicone/ Tallowtrimonium Chloride/Nonoxynol-10 | 2.00 |
| 16- FM. Extract | 16- Fermented Milk Extract | 2.00 |
| 17- DMDM. Hydantoin | 17- DMDM. Hydantoin | 0.40 |
| 18- Fragrance | 18- Natural Yogurt Fragrance | 0.15 |

The second embodiment is a water-based formulation. It is made by mixing certain ingredients in stages. Probiotic bacteria will be found in the fermented milk extract and whey protein concentrate but it is contemplated that additional specific probiotic bacteria will be supplemented in the final step in dry form:

Part A is made by dry-blending the Cellosize HEC 52000H, Whey Protein, and Kytamer P.C. in a powder blender using vigorous agitation to disperse. The powder is then mixed with the DI water in a suitable kettle. This is then mixed for twenty (20) to thirty (30) minutes at room temperature. While mixing, heat water to 73 C.-77 C. Cover the vessel. Maintain temperature and decrease speed of mechanical mixing (avoid excessive air tramping). Once Polymers are completely hydrated and a free lumps viscous gel is obtained slowly add Glucquat 125. Mix to uniformity.

Separately, to create Part B, heat Promulgen D, Stearyl Alcohol, Cetyl Alcohol, Lambent F-100, Incroquat Behemyl TMS, Abil OSW-12 and Brij 72 to 75-80 C. This procedure requires the use of high-torque impeller. Once free lumps gel is obtained heat part A at 75-80 C. When part A&B are at 75 C.-80 C., emulsify by adding part B into A. Mix to uniformity. Maintain temperature and mixing conditions for 15 minutes approximately. Cover the Main Batch in order to avoid loose water for evaporation. When the emulsion is completed start decreasing the mechanical mixing speed. Mix and cool the batch to 35 C.-40 C. Slowly add one by one ingredients Tritisol, Cetylsil Basics, D.C. 929 Cationic Emulsion, FM. Extract and DMDM. Hydantoin to the batch. Mix well to uniformity. When a uniform product is obtained, mix and cool the main batch below 35 C. Continue mixing and add Natural Yogurt Fragrance. Mix well. Q.S. the batch to final weight. Mix to uniformity.

Note: using a very slow mechanical mixing makers the mixing and cooling process to avoid air tramping. During the preparation of part A (Polymers Hydration) it is important to control temperature to prevent burning and denaturalization of the whey protein.

The ingredients listed in Examples 1 and 2 are the preferred embodiments of the invention. However, other ingredients are contemplated and may be substituted for the specific ingredients selected. Those of skill in the art of hair product formulation reference the International Cosmetic Ingredient Handbook for approved ingredients in the various categories of ingredients used to formulate hair products for consumer use.

For example, PEG 200, Behentrimonium Chloride, Steapyrium Chloride, Stearalkonium Chloride, Cetrimonium Chloride, Polyquaternium-7, Polyquaternium-11, Quaternium-79 Hydrolyzed Wheat (natural from wheat), Quaternium-79 Hydrolyzed Soy (natural from soy), and Stearamidopropyl Dimethylamine are conditioning agents. Other conditioning agents that would be suitable and easily formulated without undue experimentation by those in the art are Acetamide MEA, Alfalfa, Ceteth-2, Cetyl Alcohol, Cetrimonium Bromide or Chloride, Cetyldimonium Chloride, Cocamide DEA, Cocamidopropyl Betaine, Cocamidopropyl Hydroxysultaine, Caprylyl Pyrrolidone, Colaquat L-35, Dimethicone, Dicetyldimonium Chloride, Dimethyl Lauramine Isostearate, Dimethyl Stearamine, Guar Hydroxypropyltrimonium Chloride, Hydrolyzed Wheat Amino Acids, Keratin Protein, Lineolamido Propyl Ethydimonium Ethosulfate, Palm Kernelamide DEA and MEA, Panthenol, Sage Extract, Sodium Myristoyl Sarcosinate, Surfactant, Polyquaternium-4, Polyquaternium-10 and other compounds in the Polyquaternium family. The examples of conditioning agents above are by no means a complete list of all contemplated potential conditioning agents—other similar compounds would be known to those of skill in the art.

Certain emulsifying agents were also selected such as Glyceryl Stearate and PEG-100 Stearate, Cetyl Esters, Glycol Distearate, Cetearyl Alcohol and Ceteareth-20, Cetyl Alcohol, Stearyl Alcohol, Trideceth-10 Phosphate and Behenyl Alcohol. Other emulsifying agents that would be suitable and easily formulated without undue experimentation by those in the art are Behenyl Dimethylamine Oxide, Cetearyl Alcohol, Dimethyl Lauramine Isostearate, Dimethyl Stearamine, Glyceryl Monostearate, Polysorbate 80 and other compounds in the Polyethylene Glycol family. The examples of emulsifying agents above is by no means a complete list of all contemplated potential emulsifying agents—other similar compounds would be known to those of skill in the art.

*Olea Europaea* (Olive) Fruit Oil was selected as an emollient in the preferred embodiment. Other emollients that would be suitable and easily formulated without undue experimentation by those in the art are Ceteareth—5, Prunus Amygdalus Dulcis (Sweet Almond Oil), Buxus Chinensis (Jojoba Oil), Laureth—3, Lecithin, Lime Oil, Methyl gluceth-20, PEG-40 and Castor Oil, Avocado Oil, Safflower Oil (*Carthamus tinctorius*), Emu Oil, Soybean Oil and Sesame Oil. The examples of emollients above is by no means a complete list of all contemplated potential emollients—other similar compounds would be known to those of skill in the art.

Certain preservatives were also selected such as Methylparaben, Propylparaben and Phenoxyethanol. Other preservatives that would be suitable and easily formulated without undue experimentation by those in the art are Diazolidinyl Urea, Isopropylparaben, Isobutylparaben, Methylisothiazolinone and Methylchloroisothiazolinone. This is by no means a complete list of all contemplated preservatives—other similar compounds would be known to those of skill in the art.

The antistatic agents Polyquaternium-7, Quaternium-79 Hydrolyzed Soy and Quaterinium-79 Hydrolyzed Wheat were used in the preparation of the preferred embodiment. Other antistatic agents that would be suitable and easily formulated without undue experimentation by those in the art are Cocamidopropyl Hydroxysultaine, Lineolamido Propyl Ethydimonium Ethosulfate, Myristalkoniuum Chloride, Quaternium Compounds, Sodium Isoethionate and other compounds in the Polyquaternium family. This is by no means complete—other similar compounds would be known to those of skill in the art.

Disodium EDTA was chosen as the chelating agent. Other chelating agents that would be suitable and easily formulated without undue experimentation by those in the art are Sodium EDTA, Trisodium EDTA, Tetrasodium EDTA and Hampene NA. This is by no means complete—other similar compounds would be known to those of skill in the art.

Repair agents are contemplated as possible components of the invented haircare compositions and could be included and easily formulated without undue experimentation by those in the art. Such ingredients are Guar Hydroxypropyltrimonium Chloride and Hydrolyzed Wheat Protein with Wheat Oligosaccharides. This is by no means complete—other similar compounds would be known to those of skill in the art.

Water, glycerin and panthenyl hydroxypropyl steardimonium chloride were also chosen as the humectants in the preferred embodiments. Other humectants that would be suitable and easily formulated without undue experimentation by those in the art are Butylene Glycol, Hyaluronic Acid, Panthenol, Panthenyl ethyl ether, Sodium PCA and Sorbitol. This is by no means complete—other similar compounds would be known to those of skill in the art.

The viscosity agents Cetearyl Alcohol and Ceteareth-20, Cetyl Esters and Polyquaternium-11 were also selected. Other viscosity or volume enhancing agents that would be suitable and easily formulated without undue experimentation by those in the art are Ammonium Xylene Sulfonate, Cocamide DEA, Sodium Chloride and Tea-Dodecylbenzenesulfonate. This is by no means complete—other similar compounds would be known to those of skill in the art.

The preferred embodiment also contains the shine agent Amiodimethicone and Tridecth-12 and Cetrimonium Chloride. Other shine agents that would be suitable and easily formulated without undue experimentation by those in the art are Aloe Vera Gel, Lavender Oil and PEG-40 and Castor oil. This is by no means complete—other similar compounds would be known to those of skill in the art.

Dimethylpabamidopropyl Laurdimonium Tosylate and Glycol Stearate was added as a sunscreening agent. Other sunscreens that would be suitable and easily formulated without undue experimentation by those in the art are Benzophenone-3, Benzophenone-4, Octyl Dimethyl PABA and Geranium Oil. This is by no means complete—other similar compounds would be known to those of skill in the art.

Acetamide MEA was added as a component to exfoliate hair follicles. Another exfoliating agent that would be suitable and easily formulated without undue experimentation by those in the art is Lactic Acid. This is by no means complete—other similar compounds would be known to those of skill in the art.

The protein-cleaving enzyme Papain was used in place of traditional surfactants. Surfactants that would be suitable and easily formulated without undue experimentation by those in the art are Sodium Lauryl Sulfate, Ammonium Lauryl Sulfate, Ammonium Cocoyl Isothionate, Disodium Laureth Sulfosuccinate and Sodium Isostearoyl Lactylate.

This is by no means complete—other similar compounds would be known to those of skill in the art.

Any known fragrance—natural or synthetic—could be substituted for the fragrance elements set forth in the embodiments.

The probiotic bacteria *Lactobacillus rhamnosus, Lactobacillus casei, Lactobacillus plantarum, Lactobacillus acidophilus, Bifidobacterium longum, Bifidobacterium breve, Pediococcus, Acidilactici* and *Lactococcus diacetylactis* were selected as supplemental probiotic bacteria in the anhydrous embodiment. Other probiotic bacteria are contemplated as part of the invention and could be easily add to a disclosed formulation without undue experimentation by those in the art. These include other strains from the *Lactobacillus* family including *L. brevis, L. bulgaricus, L. fermentum, L. caucasicus, L. helveticus, L. lactis, L. plantarum* and *L. reuteri*; from the *Bifidobacterium* family including *B. bifidum* (lactis) *B. infantis, B. licheniformis* and *B. subtilus*; from the *Streptococcus* family including *S. cremoris, S. faecium, S. infantis* and *S. thermophilus*; and other strains including *Enterococcus faecium, Leuconostoc cremoris, Saccharomyces florentinus*.

This invention also contemplates the use of "prebiotics" to assist in sustaining the probiotic bacteria by including suitable ingredients to maintain a nutritive environment in the composition. Such ingredients are known and include Soy Oligosaccharides, Fructo-Oligosaccharides, Isomalto-Oligosaccharides, Xylo-Oligosaccharides, Transgalacto-Oligosaccharides, Pyrodextrins, Lactulose, Isomalto-Oligosaccharides, and Insulins.

Product Testing

Hair care compositions as set forth in the above embodiments have been subjected to a range of testing by numerous individuals with a variety of hair types. Testing included comparisons to other commercially successful hair care products. Tests were conducted on both a blind and non-blind basis. Participant's, (and in some cases, on-hand stylist's) comments were recorded and the following results were evidenced.

Trial 1: A Blind In-Salon Test

Trial number 1 is a test between the anhydrous embodiment composition (Example 1 above) and a leading commercially available luxury hair care treatment (Sample B). To ensure accuracy of the results, the samples were tested blind so as to avoid any branding bias. The objective of the test was to compare the performance and effectiveness of the samples on hair both during and after application and styling (i.e. blow drying, air drying, curling, straightening, etc.).

Prior to testing, the hair was thoroughly washed with a commercially successful clarifying shampoo and towel dried. A hair stylist then applied embodiment hair care composition (Example 1) to one side of the participant's head and the commercially available luxury hair care treatment (Sample B) to the other side of the head. Each product was evenly distributed on its respective side paying careful attention to maintaining the separation of the samples. Both products were allowed to remain in the hair for 20 minutes before the participant was instructed to rinse, comb and self-style hair in the usual manner.

Participants were asked to compare hair characteristics for both the left and right side of the head throughout the test process. A product's quality was determined by comparing responses to questions focusing on the following: overall look and feel of each product sample before application; application on wet, cleansed hair; texture and feel of each product on scalp and hair; rinse-ability of each product; ease during styling, overall impressions post styling (i.e. comparison of each product's ability to, eliminate frizz and fly-aways, promote shine and overall appearance of vitality and body in the hair).

Initially, Sample B exhibited a more favorable response, while hair treated with Example 1 was described as greasy and thick in texture, hair treated with Sample B was much lighter. However, perception changed upon the wetting and rinsing of each side of the head. At this stage, the side treated with Sample B remains lighter and cleaner, but this effect is no longer preferred. Example 1's substantial texturing effect has become the desired effect, due its ability to enhance the body and style of the hair. The side treated with Example 1 also resulted in sleeker hair with less fly-aways.

In the end, both participant's and stylist's evaluations and comments suggested that Example 1 (embodiment haircare composition) outperformed Sample B (commercially available luxury hair care treatment).

Trial 2: An At-Home Blind Test

Trial number 2 was also a comparison of an embodiment hair care composition (Example 1) and a leading hair care treatment (Sample C). To ensure the accuracy of the results, participants were given unmarked samples and instructions guiding them how to apply each sample. The objective of the test was to compare the performance and effectiveness of the samples on an individual's hair both during and after application.

Prior to testing, the hair was thoroughly washed with a commercially successful clarifying shampoo and towel dried. Participant then applied embodiment hair care composition (Example 1) to one side of her head and the commercially available luxury hair care treatment (Sample C) to the other side of her head. Participants were instructed to leave in the hair for 20 minutes before rinsing, combing and self-styling hair in their usual manner.

Participants were asked questions focusing on the following: overall look and feel of each product sample before application; application on wet, cleansed hair; texture and feel of each product on scalp and hair; rinse-ability of each product; ease during styling, overall impressions post styling (i.e. comparison of each product's ability to, eliminate frizz and fly-aways, promote shine and overall appearance of vitality and body in the hair).

In the majority of instances, Sample C was described as pleasant, light, creamy and easy to apply, while Example 1 was described as thick in texture and substantive but often, greasy, goopy or sticky and more difficult to apply than Sample C. Overall, Example 1 was perceived as harder to rinse out well. However, after rinsing and styling, participant's overwhelmingly claimed Example 1 more successful in many respects including: repairing split ends, smoothing hair, producing shine, silkiness, body and fullness and creating an especially appealing texturizing effect.

Trial 3: A Series Of Multi-Usage, Non-Blind Tests.

For several weeks participants alternated using the anhydrous embodiment (Example 1) in the following ways:

Test 1. As an intensive, pre-shampoo nutritive treatment a) on dry hair.—Participant applied a quarter sized amount of the composition on dry, unwashed hair, massaged onto the scalp, coating the entire length of the hair shaft from root to end and combing through. The composition was left on the hair for a minimum of five minutes and a maximum of 30 minutes. Hair was then washed with a leading commercially available shampoo and then blown dry using finger tousle and a hairbrush.

Results were exceptionally favorable and showed healthy, shiny hair without the presence of flyaways. The concentrated quality of the composition was found quite appealing as less of it was required for use.

b) on dampened hair—Similar to a) above, participant applied a quarter sized amount of the composition but on wetted hair, massaged onto the scalp, coating the entire length of the hair shaft from root to end and combing through. The composition was left on the hair for a minimum of five minutes and a maximum of 30 minutes. Hair was then washed with a leading commercially available shampoo and then blown dry using finger tousle and a hairbrush.

Results were also favorable, showing shiny hair without the presence of flyaways. The composition was found quite appealing as less of it was required for use.

Test 2. As an intensive, post-shampoo nutritive treatment.—As in previous tests, embodiment haircare composition was left on the hair for 10-20 minutes after cleansing with a leading commercially available shampoo. It was then rinsed styled in the usual manner.

Again, results were favorable. Upon application, the embodiment formulation seemed to bond well to the hair, melt easily into it and to detangle and smooth immediately. The longer the embodiment formulation remained on the hair, the more apparent were the results. Often, almost half the usual amount of time was required to blow hair dry and hair was easier and quicker to run a straight iron through. Hair was found to be very soft, pliable and silky when air-dried and especially after being blown straight. Overall, hair was described as soft, smooth, very shiny, full and thicker with less flyways than usual.

Test 3. As a post shampoo, leave-in, nutritive aid styling aid.—The composition was applied intermittently over several weeks as a styling aid. A dime size amount of the compositions was applied to washed, styled hair and finger combed through. Sometimes repeated applications of the product were used before the hair was washed.

In this test, the composition performed well as a pomade/texturizer/protective coating in the hair, reportedly growing less dirt Trial 4: A Series of Non-Blind At-Home Tests This trial was a take-home test using a variety of usage methods and comparing the anhydrous embodiment composition (Example 1) with the commercially available hair care treatments of each participant's choice. The objectives of these tests were 1) to illustrate the utility and performance of Example 1 when applied to hair treated with different commercially available shampoos, and 2) to illustrate the utility and performance of Example 1 with varied application.

Test 1: Embodiment haircare composition with color-treat shampoo—This test utilized commercially successful shampoos designed for color treated hair. Participants thoroughly cleansed their hair with ther selected shampoo. Hair was towel dried and combed to remove tangles. Example 1 was then applied liberally to hair beginning with the ends and ending with a vigorous massage into the scalp. Hair was covered with a towel or plastic cap and Example 1 remained in the hair for 20 minutes. Hair was thoroughly rinsed and dried styled as usual.

At this stage some participants experienced a warm tingling sensation of the scalp. After air-dry/finger-comb styling—test results were described as softer, shinier, and fuller with less fly-aways. A similar result occurred with blow-dry styling with slightly less fullness described.

Test 2: After both shampoo and conditioner—This test utilized both a commercially successful shampoo and a daily conditioner of each participant's choice prior to application of embodiment haircare composition (Example 1).

Hair was cleansed with the shampoo. The daily conditioner was applied to wet hair and rinsed after 5 minutes. After shampooing and conditioning, a quarter size amount of Example 1 was applied to the hair. Product was left on uncovered hair for 1 hour. Hair was thoroughly rinsed, dried and either air or blow dried. Results were the same as Test 1.

Test 3: Embodiment haircare composition as a pre-treatment—In this test Example 1 was applied as a pre-treatment product as opposed to the previous two tests where it was used in a post treatment context. The unwashed hair air was slightly dampened (unlike the previous tests where hair was saturated with water). A quarter size amount of Example 1 was applied to hair starting at the root and working through to the ends. Example 1 remained on uncovered hair for approximately 20 to 45 minutes before being washed and conditioned with commercially successful hair care products. Hair was blown dry either with a brush or using finger tousle, or was air dried.

Applying Example 1 prior to shampoo and conditioner was preferred to the post-treatment application method used in Tests 1 and 2. Hair exhibited no tangles and was incredibly smooth and shiny without the presence of fly-aways.

Trial 5: A Non-Blind Test

In this trial the hydrous embodiment (Example 2) was used as a post-shampoo treatment.

Participant cleansed hair with their shampoo of choice and then applied composition and left it on the hair for 10 to 30 minutes. Hair was then rinsed and blown or towel/air dried. During application, less of the coating and detangling effects occurred than with the anhydrous composition. However, after drying hair was noticeably softer.

I claim:

1. A hair treatment composition comprising: a conditioning agent, an emulsifier, a humectant and at least one type of probiotic bacteria, wherein the composition is essentially anhydrous.

2. The hair treatment composition according to claim 1 in which the probiotic bacteria is selected from the group consisting of *Lactobacillus rhamnosus, Lactobacillus casei, Lactobacillus plantarum, Lactobacillus acidophilus, Rifidobacterium longum, Bifidobacterium breve, Pedicoccus acidlactlci* and *Lactococcus diacetylactis*.

3. The hair treatment composition according to claim 1 wherein the composition is applied as a pre-shampooing treatment.

4. The hair treatment composition according to claim 1 wherein the composition is applied as a post-shampooing treatment.

5. The hair treatment composition according to claim 1 wherein the composition is applied as a leave in treatment.

6. The hair treatment according to claim 1 wherein the conditioning agent comprises about 80% PEG-200, the emulsifier comprises about 1% glyceryl stearate SE, the humectant comprises about 5% glycerin.

7. The hair treatment composition according to claim 6 further comprising dry milk and whey protein concentrate.

8. A method of treating hair comprising applying the composition of claims 1, 2, 6 or 7 to the hair.

9. The method according to claim 8, wherein the composition is applied as a pre-shampooing treatment.

10. The method according to claim 8 wherein the composition is applied as a post-shampooing treatment.

11. The method according to claim 8 wherein the composition is applied as a leave in treatment.

* * * * *